(12) United States Patent
McQueen et al.

(10) Patent No.: US 8,308,692 B2
(45) Date of Patent: Nov. 13, 2012

(54) INTRODUCER FOR USE IN INSERTING A MEDICAL DEVICE INTO A BODY VESSEL AND METHOD FOR SAME

(75) Inventors: Amy McQueen, Bloomington, IN (US); Arman H. Valaie, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 964 days.

(21) Appl. No.: 12/203,211

(22) Filed: Sep. 3, 2008

(65) Prior Publication Data
US 2010/0057009 A1 Mar. 4, 2010

(51) Int. Cl.
*A61M 5/178* (2006.01)
(52) U.S. Cl. .......... 604/167.02; 604/164.03; 604/167.06
(58) Field of Classification Search ............. 604/164.03, 604/167.01–167.03, 167.06, 93.01
See application file for complete search history.

(56) References Cited

U.S. PATENT DOCUMENTS

| | | |
|---|---|---|
| 2,321,336 A | 6/1943 | Tondreau |
| 2,416,391 A | 2/1947 | Hixson |
| 2,844,351 A | 7/1958 | Smith |
| 3,185,179 A | 5/1965 | Harautuneian |
| 3,304,934 A | 2/1967 | Bautista |
| 3,329,390 A | 7/1967 | Hulsey |
| 3,599,637 A | 8/1971 | Schwartz |
| 4,000,739 A | 1/1977 | Stevens |
| 4,016,879 A | 4/1977 | Mellor |
| 4,063,555 A | 12/1977 | Ulinder |
| 4,243,034 A | 1/1981 | Brandt |
| 4,311,137 A | 1/1982 | Gerard |
| 4,314,555 A | 2/1982 | Sagae |
| 4,424,833 A | 1/1984 | Spector et al. |
| 4,540,411 A | 9/1985 | Bodicky |
| 4,580,573 A | 4/1986 | Quinn |
| 4,610,665 A | 9/1986 | Matsumoto et al. |
| 4,610,674 A | 9/1986 | Suzuki et al. |
| 4,626,245 A | 12/1986 | Weinstein |
| 4,629,450 A | 12/1986 | Suzuki et al. |
| 4,798,594 A | 1/1989 | Hillstead |
| 4,895,565 A | 1/1990 | Hillstead |
| 4,929,235 A | 5/1990 | Merry et al. |
| 4,932,633 A | 6/1990 | Johnson et al. |
| 4,978,341 A | 12/1990 | Niederhauser |

(Continued)

FOREIGN PATENT DOCUMENTS

EP 0344907 B1 12/1989

(Continued)

*Primary Examiner* — Nicholas Lucchesi
*Assistant Examiner* — Rebecca E Eisenberg
(74) *Attorney, Agent, or Firm* — Brinks Hofer Gilson & Lione

(57) ABSTRACT

In at least one embodiment of the present invention, an introducer for use in inserting a medical device into a body vessel of a patient is provided. The introducer comprises a housing having a proximal opening, a distal opening and a chamber extending therebetween. A seal in diaphragm form is disposed in the chamber. The seal is formed of polymeric material having a first phase transition temperature higher than about body temperature and a second phase transition temperature that is less than the first phase transition temperature but is greater than about room temperature. The seal is in a first configuration and has an opening formed therethrough when at about room temperature for advancing the medical device through the seal. The seal self-configures to a second configuration when at a temperature of at least the second phase transition temperature for obstructing the body fluid from flowing through the opening of the seal.

21 Claims, 4 Drawing Sheets

U.S. PATENT DOCUMENTS

| | | |
|---|---|---|
| 5,000,745 A | 3/1991 | Guest et al. |
| 5,006,113 A | 4/1991 | Fischer |
| 5,009,391 A | 4/1991 | Steigerwald |
| 5,053,013 A | 10/1991 | Ensminger et al. |
| 5,066,285 A | 11/1991 | Hillstead |
| 5,102,395 A | 4/1992 | Cheer et al. |
| 5,125,903 A | 6/1992 | McLaughlin et al. |
| 5,154,701 A | 10/1992 | Cheer et al. |
| 5,158,553 A | 10/1992 | Berry et al. |
| 5,167,637 A | 12/1992 | Okada et al. |
| 5,176,652 A | 1/1993 | Littrell |
| 5,211,370 A | 5/1993 | Powers |
| 5,242,413 A | 9/1993 | Heiliger |
| 5,256,150 A | 10/1993 | Quiachon et al. |
| 5,267,966 A | 12/1993 | Paul |
| 5,304,156 A | 4/1994 | Sylvanowicz et al. |
| 5,350,363 A | 9/1994 | Goode et al. |
| 5,350,364 A | 9/1994 | Stephens et al. |
| 5,376,077 A | 12/1994 | Gomringer |
| 5,395,349 A | 3/1995 | Quiachon et al. |
| 5,395,352 A | 3/1995 | Penny |
| 5,409,463 A | 4/1995 | Thomas et al. |
| 5,484,418 A | 1/1996 | Quiachon et al. |
| 5,538,505 A | 7/1996 | Weinstein et al. |
| 5,613,956 A | 3/1997 | Patterson et al. |
| 5,643,227 A | 7/1997 | Stevens |
| 5,653,697 A | 8/1997 | Quiachon et al. |
| 5,702,370 A | 12/1997 | Sylvanowicz et al. |
| 5,779,681 A | 7/1998 | Bonn |
| 5,833,706 A | 11/1998 | St. Germain et al. |
| 5,895,376 A | 4/1999 | Schwartz et al. |
| 5,935,122 A | 8/1999 | Fourkas et al. |
| 6,004,280 A | 12/1999 | Buck et al. |
| 6,086,570 A | 7/2000 | Aboul-Hosn et al. |
| 6,152,144 A | 11/2000 | Lesh et al. |
| 6,183,443 B1 * | 2/2001 | Kratoska et al. ......... 604/164.03 |
| 6,197,016 B1 | 3/2001 | Fourkas et al. |
| 6,221,057 B1 | 4/2001 | Schwartz et al. |
| 6,276,661 B1 | 8/2001 | Laird |
| 6,416,499 B2 | 7/2002 | Paul, Jr. |
| 6,562,049 B1 | 5/2003 | Norlander et al. |
| 6,610,031 B1 | 8/2003 | Chin |
| 6,981,966 B2 | 1/2006 | Green et al. |
| 2003/0144670 A1 | 7/2003 | Pavcnik et al. |
| 2003/0187397 A1 * | 10/2003 | Vitali ...................... 604/167.02 |
| 2003/0216771 A1 | 11/2003 | Osypka et al. |
| 2005/0096605 A1 | 5/2005 | Green et al. |
| 2005/0096692 A1 | 5/2005 | Linder et al. |
| 2005/0171479 A1 | 8/2005 | Hruska et al. |
| 2005/0230925 A1 * | 10/2005 | Browne et al. ................. 277/919 |
| 2007/0060911 A1 | 3/2007 | Webster et al. |
| 2007/0078395 A1 | 4/2007 | Valaie |
| 2007/0276461 A1 | 11/2007 | Andreas et al. |

FOREIGN PATENT DOCUMENTS

| | | |
|---|---|---|
| EP | 0550069 A1 | 7/1993 |
| EP | 0755694 A1 | 1/1997 |
| EP | 1374942 A1 | 1/2004 |
| WO | WO99/26682 | 6/1999 |

* cited by examiner

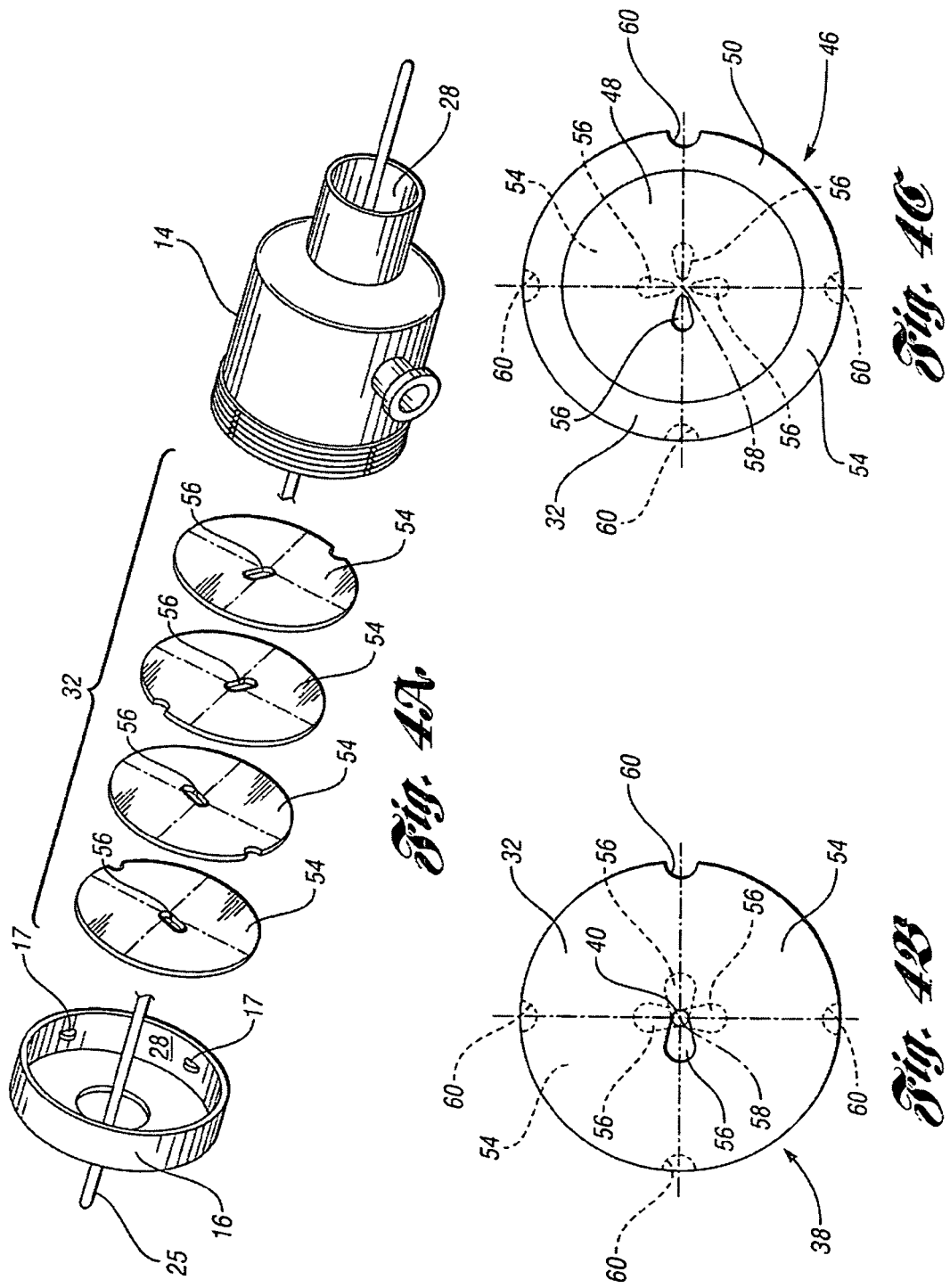

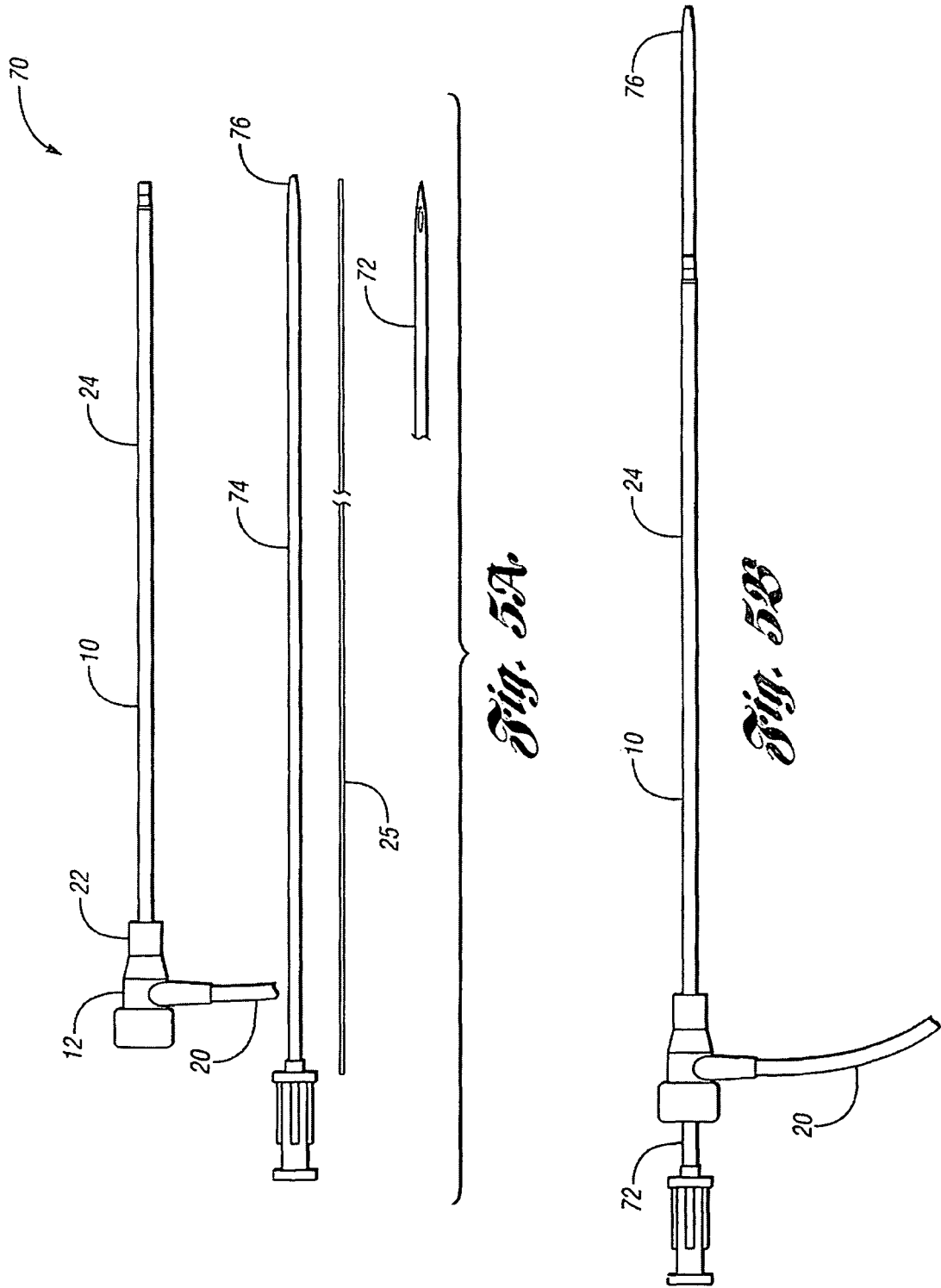

INTRODUCER FOR USE IN INSERTING A MEDICAL DEVICE INTO A BODY VESSEL AND METHOD FOR SAME

BACKGROUND OF THE INVENTION

1. Field of the Invention

The present invention relates generally to medical devices and more specifically, to an introducer having a hemostatic valve system for use in inserting a medical device into a body vessel.

2. Background

Numerous procedures have been developed in modern medicine requiring the percutaneous insertion of one or more medical devices into the vascular system of a patient. Such procedures include, for example, percutaneous transluminal coronary angioplasty (PTCA), X-ray angiographic procedures, and the alike.

The medical devices intended for use in such procedures may be introduced into the vascular system by a variety of known techniques. One widely-used technique is the Seldinger technique. In the Seldinger technique, a surgical opening is made in an artery or vein by a needle, and a guide wire is inserted into the artery or vein through a bore in the needle. The needle is thereafter withdrawn, leaving the guide wire in place. A dilator which is positioned within the lumen of the introducer device is then advanced over the guide wire into the artery or vein. Once the introducer is properly positioned within the artery or vein, the dilator is withdrawn. The introducer may then be used to insert therethrough a variety of medical interventional devices, such as for example, catheters, cardiac leads, and the alike.

In many cases, an introducer will include one or more hemostatic valve members (also referred to as check valves) for inhibiting leakage of body fluids, such as blood, back through the introducer as a medical device is inserted or withdrawn therethrough. The medical device may be for example, the dilator, a medical interventional device, e.g., catheter, or the alike. The valve member is generally positioned in a housing of the introducer, between a main body portion and an end cap. Typically, the valve member comprises an elastomeric disk having a hole formed therethrough in the center of the disk. The hole is sized to enable the medical device to be passed through the valve member, and to substantially prevent the back flow of fluids through the valve. Hemostatic valves are well known in the medical art for such purpose, and no further general discussion of the use and function of such valves is necessary for an understanding of the present invention.

Frequently, it is necessary to withdraw an inserted medical device and/or replace it with another medical device of a different diameter, or with a different type of device. In the case of replacing a previously inserted device, exchanges are normally made over a guide wire, where the old device is withdrawn over the guide wire, and the new device is thereafter inserted into the vasculature over the existing guide wire or a newly-inserted guide wire. Typically, the hemostatic valve is provided in an attempt to minimize leakage of blood back through the introducer. Such valves are dependent upon the elasticity of the valve body, and its ability to draw back upon itself to seal any gap created upon insertion or withdrawal of a device through the valve. However, the valve bodies do not always reset (e.g. due to plastic deformation of the valve body) in the proper manner following passage of the medical device and thus, additional gaps through which fluid may bleed may be created. For example, when one or more disks having a hole formed through the center are used, the hole may only partially retract back to its original size following the removal of a larger diameter catheter or other medical device. As a result, the now expanded center hole may allow substantial leakage of body fluids. Such valves may be satisfactory when there is no need to remove a device that seals the opening, however, they may be problematic when the device is removed and the center opening is created and/or enlarged.

Moreover, when larger hole opening valves are utilized, the medical device may tear the valve disk beyond the hole upon insertion. This is particularly true when a larger sized medical device is inserted. In such cases, multiple valve disks may be incorporated in order to provide a reasonable degree of confidence that the valve system will continue to provide at least some leakage control. In some cases, the damage to the valve may be so severe that it will be necessary to incorporate another type of valve, such as a Tuohy-Borst type valve, into the introducer.

Similarly, when smaller hole opening valves are utilized, the valves are also subject to tearing even when smaller sized medical devices are passed therethrough. Also, small size interventional devices are often delicate, and posses little hoop strength. When such devices are passed through a small valve member, the thickness and strength of the valve member may cause damage to the delicate structure upon passage therethrough of the medical device. Moreover, when small disks are used, the clearance between the openings and the disk in the medical device can be so slight that it may be difficult to insert and or withdraw the medical device. On some occasions, additional small diameter tubing may be used to keep the valve open so that a catheter or other medical device may be passed therethrough. When additional equipment is required, such as a small diameter tube or a Tuohy-Borst valve as described, the surgeon's hands and attention may be unduly distracted at the very time when all possible focus should be on the major task at hand.

Accordingly, further improvements and enhancements are needed for an introducer that includes a hemostatic valve system, which provides an efficient seal and avoids at least some of the problems encountered with current art seals.

BRIEF SUMMARY OF THE INVENTION

In satisfying the above need and overcoming the above and other drawbacks and limitations of the known technology, the present invention provides an introducer for use in inserting a medical device into a body vessel of a patient. The introducer comprises a housing that has a proximal opening and a distal opening. Extending between the proximal and distal openings is a chamber. A seal is disposed in the chamber and has a diaphragm form. Forming the seal is polymeric material having a first phase transition temperature and a second phase transition temperature. The first phase transition temperature is higher than about body temperature and the second phase transition temperature is less than the first phase transition temperature but is greater than about room temperature. In a first configuration is the seal having an opening formed therethrough when at about room temperature for advancing the medical device through the seal for insertion into the body vessel. When at a temperature of at least the second phase transition temperature, the seal self-configures to a second configuration for obstructing body fluid from flowing through the opening of the seal.

In one aspect, the introducer further includes a sheath that defines a conduit. The sheath extends distally from the distal opening of the housing for insertion into the body vessel. Shape memory polymers comprise the polymeric material.

In at least one other embodiment of the present invention, an introducer kit for use in inserting a medical device into a body vessel of a patient is provided. The kit comprises the introducer as discussed in the foregoing paragraphs and a guide wire for positioning in the body vessel. The sheath of the introducer is for advancing along the guide wire for insertion into the body vessel.

In at least one other embodiment of the present invention, a method for inserting a medical device into a body vessel of a patient is provided. The method comprises positioning a distal portion of a guide wire in the body vessel. A dilator is inserted through an opening formed through a seal of an introducer. The introducer includes a sheath extending distally therefrom that receives the dilator. The seal is in diaphragm form. Shape memory polymers form the seal and have a first phase transition temperature and a second phase transition temperature. The first phase transition temperature is higher than about body temperature and a second phase transition temperature is less than the first phase transition temperature but is greater than about room temperature. The seal is below the second phase transition temperature and is in a first configuration. The dilator and the sheath are cooperatively advanced along the guide wire for inserting the sheath into the body vessel. The seal is heated to at least the second phase transition temperature where the seal self-configures to a second configuration to obstruct body fluid from flowing through the opening of the seal.

Further objects, features, and advantages of the invention will become apparent from consideration of the following description and the appended claims when taken in connection with the accompanying drawings.

BRIEF DESCRIPTION OF THE DRAWINGS

FIG. 4a is an exploded view of a proximal portion of an introducer in accordance with another embodiment of the present invention;

FIG. 4b is a plan view of the seal depicted in FIG. 4a in a first configuration;

FIG. 4c is a plan view of the seal depicted in FIG. 4a in a second configuration;

FIG. 5a is an exploded view of an introducer kit in accordance with an embodiment of the present invention;

FIG. 5b is a side view of an introducer kit in accordance with an embodiment of the present invention.

DETAILED DESCRIPTION OF THE INVENTION

Figure 1:
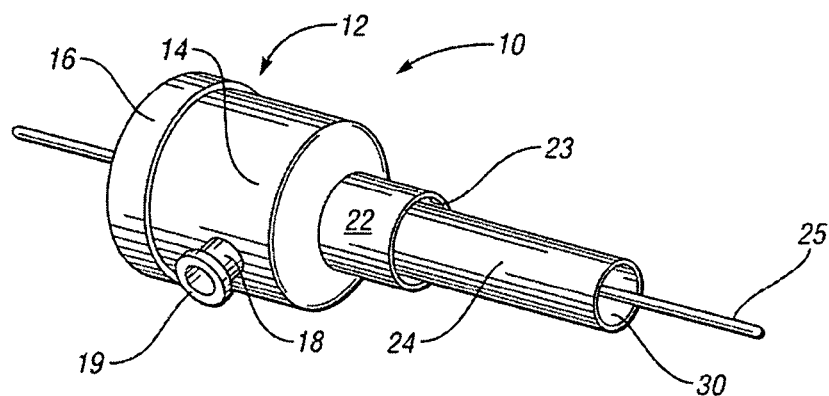
FIG. 1 is a perspective view of an introducer in accordance with an embodiment of the present invention.

Detailed embodiments of the present invention are disclosed herein. It is understood however, that the disclosed embodiments are merely exemplary of the invention and may be embodied in various and alternative forms. The figures are not necessarily to scale; some figures may be configured to show the details of a particular component. Therefore, specific structural and functional details disclosed herein are not to be interpreted as limiting but merely as a representative basis for the claims and for teaching one skilled in the art to practice the present invention.

The present invention seeks to overcome some of the problems associated with inserting a medical device into a body vessel of a patient via an introducer while providing for substantially leak-free passage of the medical device through the introducer. Preferably, the present invention provides an introducer with a hemostatic valve seal, which is at least partially formed of shape memory polymers, and a method for using the introducer for introducing a medical device into a patient's body vessel which reduces or prevents body fluid from leaking through the seal.

Shape memory polymers form polymeric material/s with the ability to sense and respond to external stimuli, e.g., temperature, pH, light, etc., in a predetermined way. Thermally induced shape memory polymers may exhibit a one-way shape memory effect due to their distinct thermal dynamics and polymer structures. Notably, this one-way memory effect differs from many shape memory alloys which can exhibit modulating shape memory effects due to the reversible nature of their grain microstructures, e.g., alternating between martensite and austenite repeatedly in response to repeated temperature changes.

In one example, shape memory polymers have polymer structures that can be considered as phase-segregated linear block copolymers having hard segments and soft segments. The hard segment, e.g., cross-linked, highly crystalline or semi-crystalline segment, acts as the frozen phase and the soft segment, e.g., amorphous or semi-crystalline segment, acts as the reversible phase. The reversible phase transformation of the soft segment is responsible for the shape memory effect. When the shape memory polymer is heated above the melting point (T(m)) or glass transition temperature (T(g)) of the hard segment, which is higher than the T(m) or T(g) of the soft segment, the material can be processed, e.g., molding, extrusion or the alike. This original shape can be memorized forming a remembered shape by cooling the shape memory polymer below the T(m) or T(g) of the hard segment. T(m) is hereinafter understood to refer to the melting temperature or melting temperature range of the polymers (or polymer segments) where the polymer crystal lattice structures are no longer stable and/or free rotation and movement of the polymers (or polymer segments) readily occurs. T(g) is hereinafter understood to refer to the glass transition temperature or glass transition temperature range, e.g., softening temperature, of the polymers (or polymer segments) where some free rotation and/or movement of the polymers (or polymer segments) can occur.

One method for forming a temporary shape is by deforming the material in the remembered shape at a temperature below the T(m) or T(g) of the hard segment but above the T(m) or T(g) of the soft segment and then cooling the material below the T(m) or T(g) of the soft segment to fix the deformed shape. The remembered or original shape is recovered by heating the shape memory polymer above the T(m) or T(g) of the soft segment, allowing at least some free rotation and/or movement of the soft segment for releasing the material from its temporary shape. Another method for setting the temporary shape involves the material in the remembered shape being deformed at a temperature lower than the T(m) or T(g) of the soft segment, resulting in stress and strain being absorbed by the soft segment. When the material is heated above the T(m) or T(g) of the soft segment, the stress and strains are relieved, e.g., via at least some free rotation and/or movement of the soft segment, and the material returns to its remembered shape. This is believed to be why the thermally induced shape memory polymers of the present invention have a one-way shape memory effect; they remember one permanent shape formed at the higher temperature, while many temporary shapes are possible at lower temperatures for which the systems do not have any memory because of the free rotation and/or movement of the soft segments.

The present invention employs polymeric material having shape memory properties to form the hemostatic valve seal of the introducer. Preferably, the temporary shape of the seal provides an opening for advancing a medical device through the seal for insertion into the patient's body vessel and the remembered shape is a swollen or expanded shape to enhance sealing performance of the seal, reducing and/or preventing leakage of body fluid through the seal.

Referring to FIG. 1, an introducer in accordance with at least one embodiment of the present invention is provided. The introducer 10 includes a housing 12. The housing 12 comprises a main body 14 and an end cap 16. Hard plastic or other suitably rigid and biocompatible material may be used to form the main body 14 and the end cap 15. The main body 14 and the end cap 15 may be joined together in any conventional fashion, such as by a screw fit or a snap fit. For example, the embodiment in FIG. 2 illustrates the main body 14 having one or more screw threads (grooves) 15 that may engage with one or more tabs 17 in the end cap 16.

The housing 12 may also include a side-arm spout 18 extending in a generally transverse direction from the main housing body 14. The spout 18 may include a lip 19 that is sized and shaped for threaded engagement or alike with a tube 20 (shown in FIGS. 5a and 5b) or other device, for use in the transmittal or aspiration of a fluid or a drug in a conventional fashion.

The distal end of the housing body 14 comprises a smaller diameter portion 22 that forms a distal opening 23. A sheath 24, which may be removable, extends distally from the small diameter portion 22 of the housing in a conventional fashion and is for being inserted into a body vessel of a patient. The sheath 24 is preferably made of a flexible, biocompatible material and defines a conduit 30 for advancing a medical device therein for introduction to and retrieval from the body vessel. In the embodiment shown, a guide wire 25 is illustrated extending through the introducer 10. Preferably, one or more of the medical devices are advanced to and from the body vessel over the guide wire 25 as is well known in the art.

Figure 2:
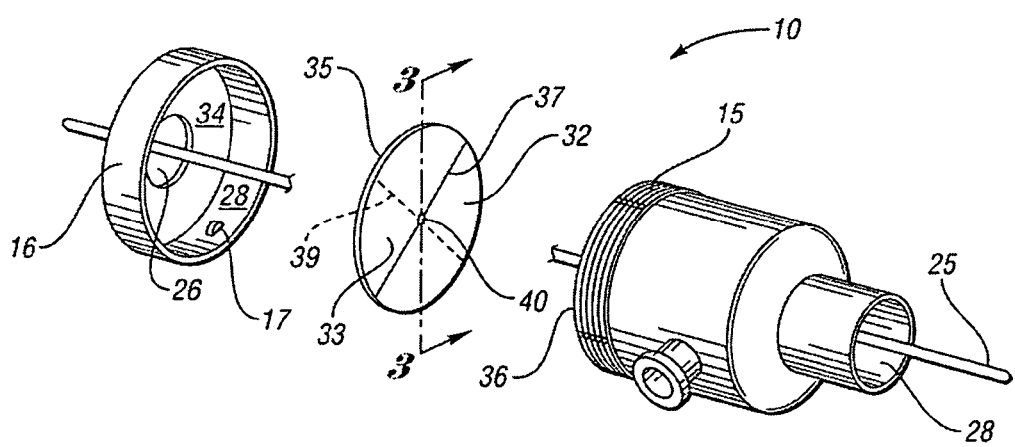
FIG. 2 is an exploded view of a proximal portion of an introducer in accordance with one embodiment of the present invention.

Also with reference to FIG. 2, the end cap 16 has a proximal opening 26 that is sized for passage of the medical device therethrough. A chamber 28 is defined by the housing 12 and extends between the proximal opening 26 and the distal opening 23.

Disposed in the chamber 28 is a hemostatic valve seal 32. The seal is made from polymeric material which is preferably compliant, e.g., elastomeric and soft with a Shore A hardness (Durometer) between about 20 to 100, and resistant to body fluid for suitable sealing characteristics. In one embodiment, the seal 32 has a form of a diaphragm and preferably extends to the inside perimeter surface of the housing 12 so that it is retained and/or constrained between an inside surface 34 of the end cap 16 and the perimeter edge 36 of the main body 14, e.g., an outer perimeter portion of the seal 32 being sandwiched between the inside surface 34 and the perimeter edge 36. In this configuration, the diaphragm form of the seal 32 may substantially obstruct body fluid from flowing past the seal 32 through the proximal opening 26 of the introducer 10.

In the embodiment illustrated, the seal 32 has a first side 33 and a second side 35 that is opposite the first side 33. The seal 32 has a first slit 37 formed therein that extends from the first side 33 and a second slit 39 formed therein that extends from the second side 35. In a first configuration 38 (shown in FIG. 3a and as will be discussed in further detail hereinafter), the slits 37 and 39 intersect to form an opening 40 which provides access through the seal 32 for advancing the medical device.

In at least one embodiment, the polymeric material of the seal 32 is comprised of shape memory polymers. Some examples of suitable polymers which may be formulated or polymerized to have shape memory effects are polyurethanes, polyester-urethanes, polyether-urethanes, polyesters, polyester-ethers, polyvinyl chlorides, silicones, and polyvinyl-alcohols. The polymeric material may include one of these types of polymers or these polymers may be blended or mixed to preferably form a relatively compliant material with good sealing capability and shape memory.

In one embodiment, the polymeric material has a first phase transition temperature, e.g., T(m) or T(g) of the hard segments of the shape memory polymers, and a second phase transition temperature, e.g., T(m) or T(g) of the soft segments of the shape memory polymers. The first phase transition temperature is higher than about body temperature and the second phase transition temperature is less than the first phase transition temperature but is greater than about room temperature. Body temperature is typically about 98.6 degrees Fahrenheit (0F) but may vary slightly depending on the well-being of the patient, preferably between about 95°-103° F. and more preferably between about 97°-101° F., and room temperature is typically about 65°-76° F. and more preferably between about 70°-72° F. In one example, the first phase transition temperature is greater than about 106° F. In another example, the second phase transition temperature is in the range of about 88-95° F.

Figure 3A:
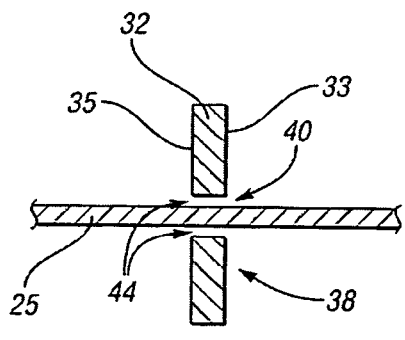
FIG. 3a is a sectional view of the seal depicted in FIG. 2 in a first configuration.

When at about room temperature and as illustrated in FIG. 3a, the seal 32 is in the first configuration 38. That is, the first configuration 38 is the temporary shape. The first configuration 38 is for advancing a medical device through the opening 40 of the seal 32 and into the conduit 30 of the sheath 24. In one embodiment, the opening 40 of the seal 32 is sized to facilitate advancing the medical device over a guide wire 42 and through the seal 32. For example, a small gap 44 may exist between the seal 32 and the guide wire 42 when the guide wire 42 is disposed through the opening 40. The gap 44 may help to reduce both resistance to advancing the medical device through the opening 40 as well as hoop stresses and strains imparted to the advancing medical device.

Figure 3B:
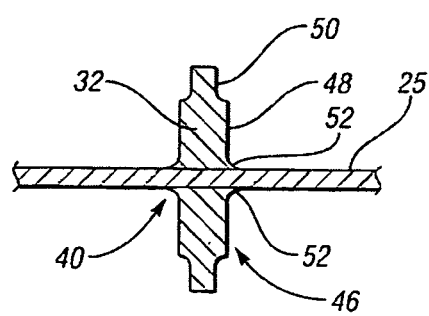
FIG. 3b is a sectional view of the seal depicted in FIG. 2 in a second configuration.

Also with reference to FIG. 3b, the seal 32 in at least one embodiment self-configures to a second configuration 46 when at a temperature of at least the second phase transition temperature due to the shape memory properties of the polymeric material. That is, the second configuration 46 is the remembered shape. The second configuration 46 preferably has a shape for restricting and/or obstructing body fluid from the patient's body vessel from flowing through the opening 40 of the seal 32, e.g., reducing or eliminating the gap/s 44.

In the example illustrated in FIG. 3b, the seal 32 in the second configuration 46 is expanded relative to the first configuration 38 to a swollen state. In particular, the seal 32 has an expanded central portion 48 about the opening 40 and an outer perimeter portion 50, which may remain substantially unexpanded due to being sandwiched and constrained between the inside surface 34 of the end cap 16 and the perimeter edge 36 of the main body 14 and/or being intentionally deformed as such during the shape memorization process. It is believed that the unexpanded outer perimeter portion 50 may further swell the expanded central portion 48 by concentrating the entire seal's volumetric expansion inwardly towards the central portion 48, e.g., via a Poisson's effect. In this configuration 46, the first and second slits 37 and 39 become compressed and restrict and/or close up the opening 40 of the seal 32. If a guide wire 25 or other medical device is disposed within the opening 40, the opening 40 will be prevented from closing up but may constrict about the guide wire 25 and/or medical device to form a compressing inner portion 52 disposed about the opening 40 to form a substantially leak-tight interface with the guide wire 25 and/or medical device.

Referring to FIGS. 4a-4c, an alternative embodiment of the seal 32 is provided. The seal 32 may include a plurality of valve members 54 that are packed together and axially aligned in the chamber 28. Each of the valve members 54 has an aperture 56 formed therethrough. In the first configuration 38, an example of which is illustrated in FIG. 4b, the opening 40 of the seal 32 is formed by axial alignment of the apertures 56 and more preferably, only partial axial alignment of the apertures 56. That is, the apertures 56 are preferably substantially non-coaxial and partially offset from the center 58 of each of the valve members 54 with only a portion of each of the apertures 56 being coaxial and centered 58. The portions of the apertures 56 that are coaxial and centered 58 form the opening 40 of the seal 32. Moreover, to ensure the substantially non-coaxial and partially offset from the center 58 positioning of the apertures 56 relative to each other, the valve members 54 may have locator features 60 which correspond to the tabs 17 of the main body 14 for defining the radial orientation of each of the valve members 54.

As described in the foregoing paragraphs, the seal 32 self-configures to the second configuration 46 when at a temperature of at least the second phase transition temperature. In the example illustrated in FIG. 4c, the swollen shape of the seal 32 in the second configuration 46 is formed by the expansion of each of the valve members 54 due the shape memory effect, thereby reducing the sizes of the apertures 56. By reducing the size of each of the apertures 56, the portions of the apertures 56 that are coaxial and centered 58 are preferably reduced or eliminated and thus, the apertures 56 may be further or completely non-coaxial and non-centered. If a guide wire 25 or other medical device is disposed through the apertures 56, the apertures 56 will still be urged to misalign but the size of the opening 40 will instead be restricted to form a substantially leak-tight interface between the seal 40 and the guide wire 25 and/or medical device.

In at least one embodiment of the present invention, the shape memory polymers are plasticized when contacted with body fluid, reducing the corresponding T(g) or T(m) of the soft segments, i.e., decreasing the temperature of the second phase transition temperature. In particular, the shape memory polymers may be formulated to have limited or controlled body fluid permeability, e.g., water permeability. For example, the water absorptivity of shape memory polyurethanes (SMPUs) is influenced by the mixed polyol blocks formed therein (e.g. urethanes may be formed from polyols and isocyanates) owing to their difference in microstructure. These blocks, e.g. soft segments, act as hydrophilic segments and are an almost amorphous loose structure which provides more space for water molecules. Once the water molecules of the body fluid are absorbed onto the SMPU, the physical mobility of these blocks increases owing to the plasticization effect, thereby decreasing the second phase transition temperature. This embodiment may offer some advantages for packaging, shipping and handling of the introducer 10 without prematurely causing the seal 32 to self-configure to the second configuration 46 due to elevated environmental temperatures outside of the patient's body.

Referring to FIGS. 5a-5b, at least one embodiment of an introducer kit for use in inserting a medical device into a body vessel of a patient is provided. The kit 70 comprises the introducer 10 and the guide wire 25 as discussed in the foregoing paragraphs. The kit 70 may also include a needle 72 for forming percutaneous access for the guide wire 25 into the body vessel. Specifically, the needle 72 may be used to form a surgical opening through the skin and into an artery or vein and the guide wire 25 may be inserted into the artery or vein through a bore in the needle 72.

In one embodiment, the kit 70 includes a dilator 74. The dilator 74 is elongated and has an outer diameter that is sized to fit through the introducer 10 including the opening 40 of the seal 32 and the conduit 30 of the sheath 24. The dilator 74 has an open distal end 76 that is tapered. When the dilator 74 is disposed through the introducer 10, the distal end 76 of the dilator 74 projects distally from the sheath 24 of the introducer 10 as illustrated in FIG. 5b. The taper open distal end 76 of the dilator 74 provides a transitional lead for the introducer 10 to facilitate insertion of the sheath 24 over the guide wire 25 into the body vessel.

Figure 6:
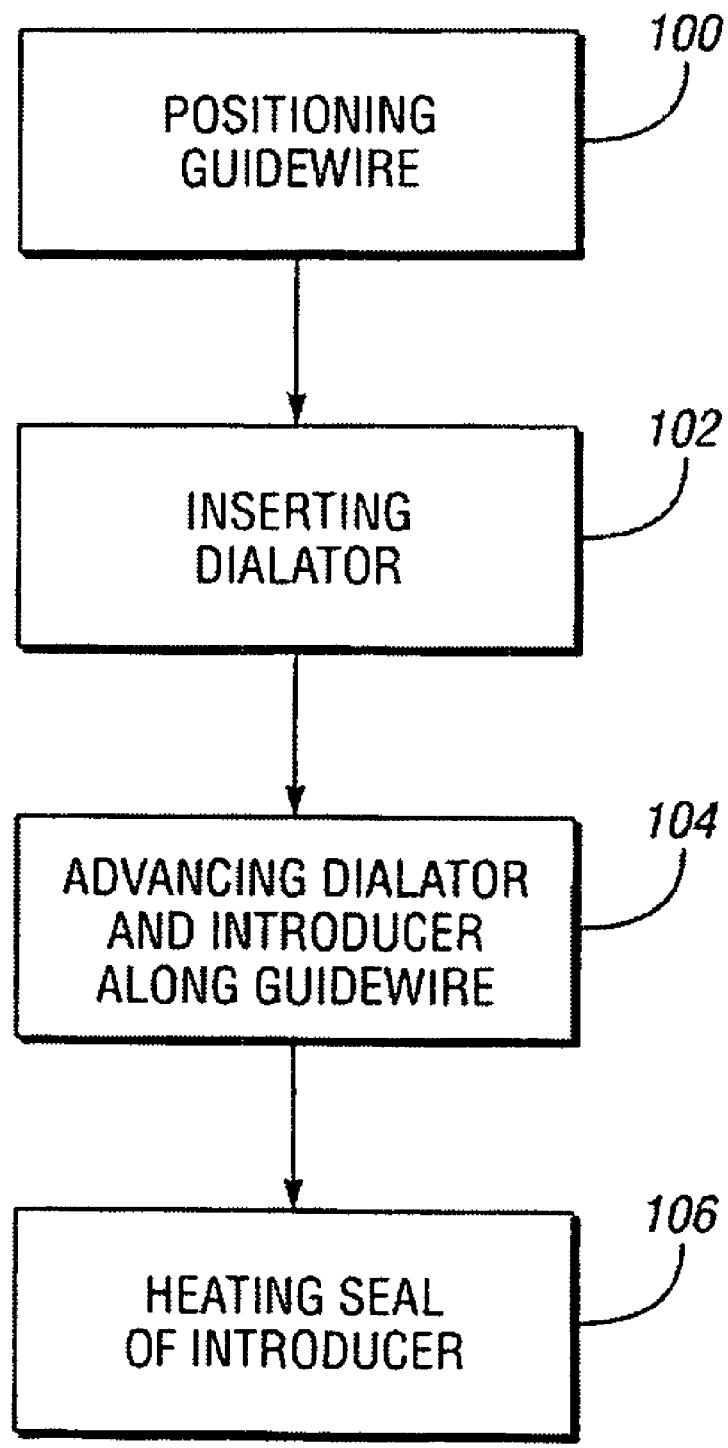
FIG. 6 is a flow chart of a method for introducing a medical device into a body vessel of a patient in accordance with an example of the present invention.

Referring to FIG. 6, a method for inserting a medical device into a body vessel of a patient in accordance with an example of the present invention is provided. The method comprises positioning a distal portion of a guide wire at 100 in the body vessel of a patient. The body vessel contains body fluid.

A dilator is inserted at 102 through an opening formed through a seal of an introducer. The introducer includes a sheath that extends distally therefrom. The dilator is received by the sheath. The seal is in diaphragm form and is formed of shape memory polymers. The shape memory polymers have a first phase transition temperature, which is higher than about body temperature, and a second phase transition temperature, which is less than the first phase transition temperature but is greater than about room temperature. The seal is in a first configuration and is below the second phase transition temperature.

The dilator and the sheath are cooperatively advanced distally along the guide wire to insert the sheath into the body vessel at 104. The seal is heated at 106 to at least the second phase transition temperature where it self-configures to a second configuration to obstruct the body fluid from flowing through the opening of the seal.

In one aspect, the step of heating the seal includes warming the seal with the body fluid.

In another aspect, the step of heating the seal to at least the second phase transition temperature includes contacting the seal with body fluid where the shape memory polymers are plasticized to reduce the second phase transition temperature.

As a person skilled in the art will readily appreciate, the above description is meant as an illustration of the implementation of the principles of the invention. This description is not intended to limit the scope for application of this invention in that the invention is susceptible to modification, variation, and change, without departing from the spirit of this invention as defined in the following claims.

The invention claimed is:

1. An introducer for use in inserting a medical device into a body vessel of a patient containing body fluid, the introducer comprising:

a housing having a proximal opening, a distal opening and a chamber extending therebetween;

a sheath defining a conduit and extending distally from the distal opening of the housing for insertion into the body vessel; and a seal in diaphragm form disposed in the chamber and formed of shape memory polymers having a first phase transition temperature higher than about body temperature and a second phase transition temperature less than the first phase transition temperature but greater than about room temperature, the seal in a first configuration having an opening formed therethrough when at about room temperature for advancing the medical device through the seal into the conduit of the sheath and the seal self-configuring to a second configuration when at a temperature of at least the second phase transition temperature for obstructing the body fluid from flowing through the opening of the seal.

2. The introducer of claim 1 wherein the first phase transition temperature is greater than about 106° F. and the second phase transition temperature is less than about the body temperature.

3. The introducer of claim 1 wherein the second phase transition temperature is in the range of about 88 to 95° F.

4. The introducer of claim 1 wherein the seal has a first side and a second side opposite the first side, the seal having a first slit formed therein extending from the first side and a second slit formed therein extending from the second side, the second slit intersecting with the first slit to form the opening.

5. The introducer of claim 4 wherein the seal is swollen in the second configuration relative to the first configuration, compressing the first and second slits to restrict a size of the opening.

6. The introducer of claim 1 wherein the seal includes a plurality of valve members packed together and axially aligned in the chamber, each of the valve members having an aperture formed therethrough, the apertures in the first configuration at least partially aligned to form the opening and in the second configuration urged to misalign to restrict a size of the opening.

7. The introducer of claim 6 wherein the apertures are substantially non-coaxial and at least partially offset from a center portion of the seal and the seal is swollen in the second configuration relative to the first configuration, reducing sizes of the apertures.

8. The introducer of claim 1 wherein the first configuration is defined by a shape of the seal while being cooled through the first phase transition temperature and the second configuration is defined by deforming the first configuration while one of being at a temperature below the second phase transition temperature and being cooled through the second phase transition temperature.

9. The introducer of claim 1 wherein the shape memory polymers are plasticized when contacted with the body fluid to reduce the second phase transition temperature.

10. The introducer of claim 1 wherein the seal is swollen in the second configuration relative to the first configuration.

11. An introducer kit for use in inserting a medical device into a body vessel of a patient containing body fluid, the kit comprising:
   a guidewire for positioning in the body vessel; and
   an introducer including:
      a housing having a proximal opening, a distal opening and a chamber extending therebetween;
      a sheath defining a conduit and extending distally from the distal opening of the housing for being advanced along the guidewire for insertion into the body vessel; and
      a seal in diaphragm form disposed in the chamber and formed of shape memory polymers having a first phase transition temperature higher than about body temperature and a second phase transition temperature less than the first phase transition temperature but greater than about room temperature, the seal in a first configuration having an opening formed therethrough when at about room temperature for advancing the medical device through the seal into the conduit of the sheath and the seal self-configuring to a second configuration when at a temperature of at least the second phase transition temperature for obstructing the body fluid from flowing through the opening of the seal.

12. The kit of claim 11 further comprising a dilator that is received into the introducer and is configured for advancing along the guidewire with the introducer to facilitate insertion of the sheath into the body vessel.

13. The kit of claim 11 further comprising a needle for forming percutaneous access for the guidewire into the body vessel.

14. The kit of claim 11 wherein the first phase transition temperature is greater than about 106° F. and the second phase transition temperature is less than about the body temperature.

15. The kit of claim 11 wherein the second phase transition temperature is in the range of about 88 to 95° F.

16. The kit of claim 11 wherein the seal has a first side and a second side opposite the first side, the seal having a first slit formed therein extending from the first side and a second slit formed therein extending from the second side, the second slit intersecting with the first slit to form the opening.

17. The kit of claim 16 wherein the seal is swollen in the second configuration relative to the first configuration, compressing the first and second slits to restrict a size of the opening.

18. The kit of claim 11 wherein the seal includes a plurality of valve members packed together and axially aligned in the chamber, each of the valve members having an aperture formed therethrough, the apertures in the first configuration at least partially aligned to form the opening and in the second configuration urged to misalign to restrict a size of the opening.

19. The kit of claim 18 wherein the apertures are substantially non-coaxial and at least partially offset from a center portion of the seal and the seal is swollen in the second configuration relative to the first configuration, reducing sizes of the apertures.

20. The kit of claim 11 wherein the shape memory polymers are plasticized when contacted with the body fluid to reduce the second phase transition temperature.

21. A method for inserting a medical device into a body vessel of a patient containing body fluid, the method comprising:
   positioning a distal portion of a guidewire in the body vessel;
   inserting a dilator through an opening formed through a seal of an introducer, the introducer including a sheath extending distally therefrom that receives the dilator, the seal in diaphragm form and formed of shape memory polymers having a first phase transition temperature higher than about body temperature and a second phase transition temperature less than the first phase transition temperature but greater than about room temperature, the seal in a first configuration below the second phase transition temperature;
   cooperatively advancing the dilator and the sheath of the introducer distally along the guidewire, inserting the sheath into the body vessel; and
   heating the seal to at least the second phase transition temperature, the seal self-configuring to a second configuration to obstruct the body fluid from flowing through the opening of the seal.

* * * * *

UNITED STATES PATENT AND TRADEMARK OFFICE
CERTIFICATE OF CORRECTION

PATENT NO. : 8,308,692 B2  
APPLICATION NO. : 12/203211  
DATED : November 13, 2012  
INVENTOR(S) : Amy McQueen et al.

Page 1 of 1

It is certified that error appears in the above-identified patent and that said Letters Patent is hereby corrected as shown below:

<u>On the Title Page</u>

Item (73), replace "Cook Incorporated," with --Cook Medical Technologies LLC,--.

Signed and Sealed this
Twenty-fourth Day of September, 2013

Teresa Stanek Rea
*Deputy Director of the United States Patent and Trademark Office*